(12) United States Patent
Gellman et al.

(10) Patent No.: US 7,041,047 B2
(45) Date of Patent: May 9, 2006

(54) METHOD AND APPARATUS FOR THE DELIVERY OF BRACHYTHERAPY

(75) Inventors: Barry N. Gellman, N. Easton, MA (US); Jozef Slanda, Milford, MA (US); Kimberly Paddock, Newton, MA (US); Douglas Godshall, Franklin, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 175 days.

(21) Appl. No.: 10/264,637

(22) Filed: Oct. 4, 2002

(65) Prior Publication Data

US 2004/0068157 A1 Apr. 8, 2004

(51) Int. Cl.
*A61N 5/00* (2006.01)

(52) U.S. Cl. .......................................... 600/3

(58) Field of Classification Search ............... 600/1–8, 600/439, 567, 562, 564; 604/106, 174, 57, 604/60, 523, 528, 95.01, 164.01, 104, 107, 604/27, 106.01, 264, 107.27, 106.07, 165.02; 606/41, 198, 33; 250/497.1, 516.1
See application file for complete search history.

(56) References Cited

U.S. PATENT DOCUMENTS

| | | | | |
|---|---|---|---|---|
| 1,867,624 A | * | 7/1932 | Hoffman | 600/567 |
| 4,402,308 A | * | 9/1983 | Scott | 600/7 |
| 4,697,575 A | | 10/1987 | Horowitz | 128/1 |
| 4,700,692 A | * | 10/1987 | Baumgartner | 600/7 |
| 4,815,449 A | | 3/1989 | Horowitz | 600/7 |
| 5,120,973 A | * | 6/1992 | Rohe et al. | 250/497.1 |
| 5,141,487 A | | 8/1992 | Liprie | 600/7 |
| 5,242,373 A | | 9/1993 | Scott et al. | 600/7 |
| 5,267,960 A | * | 12/1993 | Hayman et al. | 604/106 |
| 5,322,499 A | | 6/1994 | Liprie | 600/8 |
| 5,429,582 A | | 7/1995 | Williams | 600/2 |
| 5,498,227 A | | 3/1996 | Mawad | 600/3 |
| 5,906,574 A | * | 5/1999 | Kan | 600/7 |
| 5,924,974 A | | 7/1999 | Loffler | 600/3 |
| 5,928,130 A | | 7/1999 | Schmidt | 600/7 |
| 6,030,333 A | | 2/2000 | Sioshansi et al. | 600/3 |
| 6,059,767 A | * | 5/2000 | Noriega | 604/523 |
| 6,066,083 A | | 5/2000 | Slater et al. | 600/8 |

(Continued)

FOREIGN PATENT DOCUMENTS

WO  WO 96/14880  5/1996

(Continued)

*Primary Examiner*—Samuel G. Gilbert
(74) *Attorney, Agent, or Firm*—Mayer & Williams PC; David B. Bonham, Esq.; Keum J. Park, Esq.

(57) ABSTRACT

A brachytherapy device includes a radiation source and a multi-cannula delivery system for implantation of the radiation source into a body tissue site. The radiation source may be, for example, a substantially straight round wire, a substantially straight flat wire, a detented wire, an embossed wire, a bristled wire, a shaped resilient wire, a twisted round wire, a twisted flat wire, or a coil with or without an inner core, and is adapted for implantation into a body tissue site and for delivery of radiation to the body tissue site. The multi-cannula delivery system includes an outer cannula, an outer stylet, an inner cannula, and an inner stylet. Different configurations of the radiation source according to embodiments of the invention improve distribution of the radiation field in the longitudinal direction and resistance to migration of the radiation source inside a patient's body. The multi-cannula delivery system provides for faster and more accurate placement of the radiation source.

10 Claims, 7 Drawing Sheets

U.S. PATENT DOCUMENTS

| | | | |
|---|---|---|---|
| 6,146,322 A | 11/2000 | Papirov et al. | 600/3 |
| 6,200,256 B1 | 3/2001 | Weinberger | 600/3 |
| 6,210,316 B1 | 4/2001 | Slater et al. | 600/8 |
| 6,231,494 B1 | 5/2001 | Verin et al. | 600/1 |
| 6,235,001 B1 * | 5/2001 | O'Holloran et al. | 604/165.02 |
| 6,264,599 B1 | 7/2001 | Slater et al. | 600/7 |
| 6,270,472 B1 * | 8/2001 | Antaki et al. | 604/61 |
| 6,338,709 B1 * | 1/2002 | Geoffrion et al. | 600/3 |
| 6,402,677 B1 | 6/2002 | Jacobs | 600/7 |
| 6,409,651 B1 * | 6/2002 | Brown, III | 600/3 |
| 6,419,621 B1 * | 7/2002 | Sioshansi et al. | 600/3 |
| 6,436,026 B1 * | 8/2002 | Sioshansi et al. | 600/3 |
| 6,450,937 B1 * | 9/2002 | Mercereau et al. | 600/7 |
| 6,482,178 B1 * | 11/2002 | Andrews et al. | 604/164.01 |
| 6,494,835 B1 * | 12/2002 | Ciezki et al. | 600/439 |
| 6,497,645 B1 * | 12/2002 | Halpern | 600/3 |
| 6,572,525 B1 * | 6/2003 | Yoshizumi | 606/7 |
| 6,572,527 B1 * | 6/2003 | Steele et al. | 600/7 |
| 6,582,352 B1 * | 6/2003 | Verin et al. | 600/1 |
| 6,582,354 B1 * | 6/2003 | Ellard | 600/8 |
| 6,648,811 B1 * | 11/2003 | Sierocuk et al. | 600/7 |
| 6,652,442 B1 * | 11/2003 | Gatto | 600/3 |
| 6,669,622 B1 * | 12/2003 | Reed et al. | 600/7 |
| 6,712,816 B1 * | 3/2004 | Hung et al. | 606/41 |
| 2002/0049411 A1 | 4/2002 | Lamoureux et al. | 604/164.01 |
| 2002/0058932 A1 * | 5/2002 | Moorman et al. | 606/33 |
| 2002/0173689 A1 * | 11/2002 | Kaplam | 600/7 |
| 2003/0028067 A1 * | 2/2003 | Tarone et al. | 600/1 |
| 2004/0116767 A1 * | 6/2004 | Lebovic et al. | 600/7 |

FOREIGN PATENT DOCUMENTS

| | | |
|---|---|---|
| WO | WO 97/19706 | 6/1997 |
| WO | WO 98/01179 | 1/1998 |
| WO | WO 02/34325 A1 | 5/2002 |

* cited by examiner

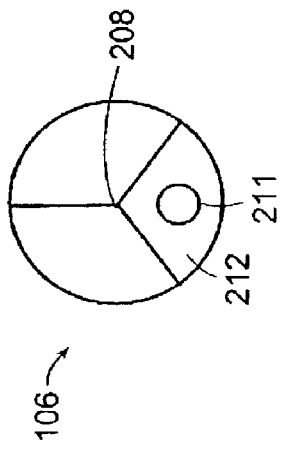
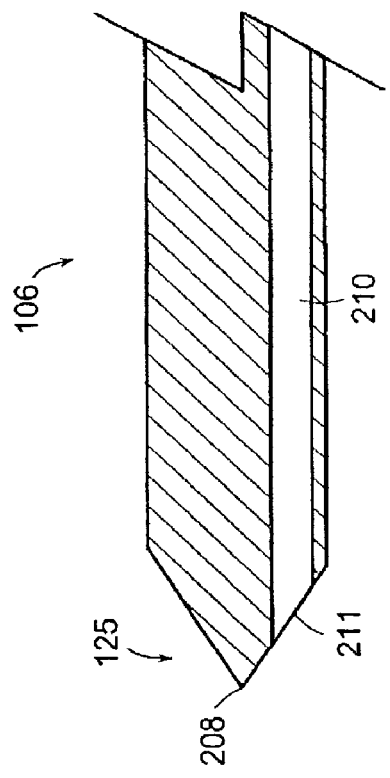
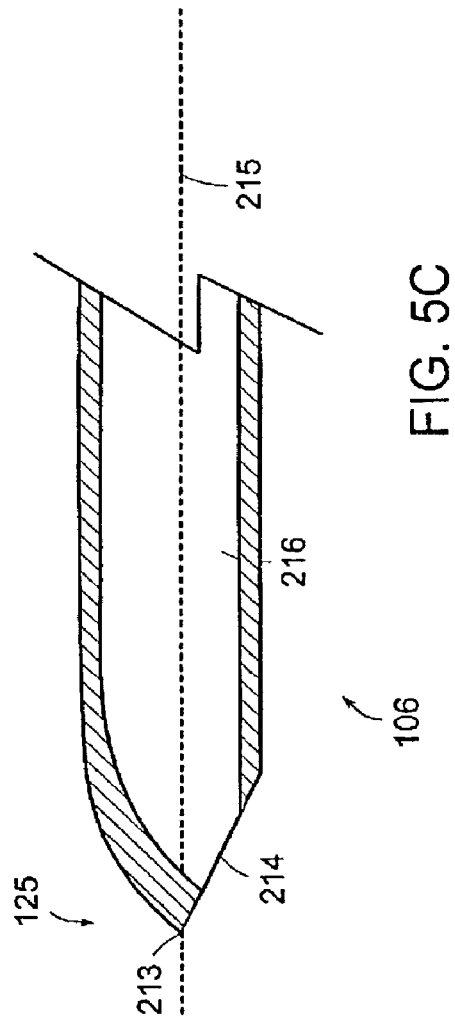

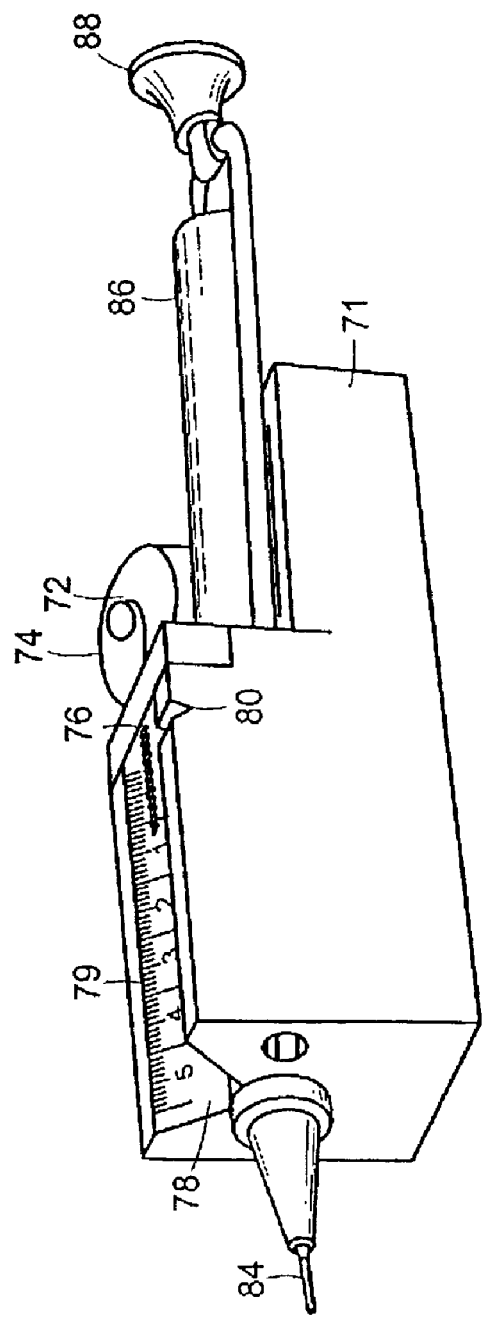
FIG. 6
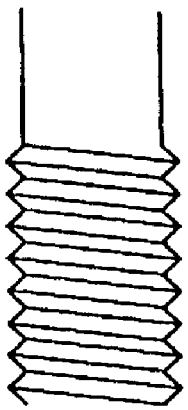
FIG. 7D
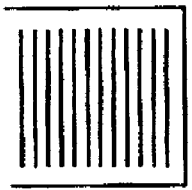
FIG. 7C
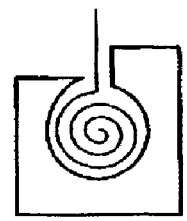
FIG. 7B
FIG. 7A

METHOD AND APPARATUS FOR THE DELIVERY OF BRACHYTHERAPY

TECHNICAL FIELD

This invention relates to the field of treatment of cancer and, more particularly, to a method and an apparatus for treating tissue through brachytherapy.

BACKGROUND OF THE INVENTION

Traditional high-dose external beam radiation treatment and prolonged low-dose radiation treatment (brachytherapy) are well-established therapies for the treatment of cancer, a malignant form of cellular proliferation. Brachytherapy is a form of radiation treatment in which a radiation source is placed into or adjacent to a malignant tumor. There are two general categories of brachytherapy: high dose rate (HDR) and low dose rate (LDR). HDR brachytherapy typically involves the placement of a high-activity radiation source adjacent to or into the malignant tumor for a limited period of time. LDR brachytherapy involves the placement of a low-activity radiation source adjacent to or into the malignant tumor for an indefinite period of time.

The implantable low activity radiation sources are typically quite expensive. In particular, the source may only be effective for radiotherapy during a relatively brief period of time during which the radioactivity is provided at a useful therapeutic level. Depending on the radioisotope used, the decay time may be as short as hours, days or weeks.

Brachytherapy devices for treatment of localized lesions such as tumors of the prostate, breast, brain, eye, liver, spleen, or the like, commonly employ radioactive "sealed source" seeds. The term "sealed source," as used herein, means that radioisotopes incorporated into a device are integral with the device and are not released from the host material of the device in the environment of usage. A typical sealed source seed includes a radiation source encapsulated within a substantially impermeable, biocompatible capsule made of, for example, titanium that is designed to prevent leakage or release of the radioisotope. The seeds are typically about 0.50 to 0.85 mm in diameter and about 4 to 10 mm long. These seeds are implanted individually at a treatment site within and/or around a lesion, typically with a medium-bore 18-gauge delivery needle.

The radiation sources used in LDR brachytherapy are radioactive isotopes. Common isotopes used are $^{103}$Pd (Palladium), $^{125}$I (Iodine), $^{198}$Au (Gold), and $^{192}$Ir (Iridium). The isotopes used in LDR brachytherapy are chosen for their low energy and short half-life. Low energy provides for limited penetration of the radiation so that the radiation effect is limited to the tumor without affecting adjacent normal tissue. A short half-life is desirable so that the radiation dose can be delivered in a reasonably brief period of time.

For $^{103}$Pd and $^{125}$I, the zone of therapeutic effect is limited to about a 1-cm diameter sphere around the seed. Typically, a three-dimensional array of seeds is used to treat a tumor. In LDR brachytherapy of prostate cancer, over 100 seeds are typically used. Because solid tumors, such as those found in prostate cancer, are viewed to be diffused, the entire organ is targeted.

Conventionally, a medical operator places multiple seeds into a three-dimensional array with a needle using a two-dimensional grid pattern, and longitudinal spacing. A needle guide called a template typically defines the two-dimensional grid. The template includes a matrix of holes, which guide the longitudinal advancement of the needles to insure their proper two-dimensional positioning in the tumor. Subsequent to establishing the two-dimensional array of needles in the tumor, the medical operator deposits the seeds along the longitudinal axis of each needle. Biocompatible spacers typically space the seeds along the longitudinal axis of the needle. The medical operator alternately inserts spacers and seeds into the needle prior to placing the needle into the tumor. To maintain the position of the line of seeds and spacers as the needle is withdrawn, the medical operator typically employs a mandrel. This leaves a line of seeds in their proper longitudinal position. The medical operator then repeats this process at the other two-dimensional grid coordinates forming the desired three-dimensional array of seeds.

LDR brachytherapy is an effective modality for treating localized malignancies, however, it is not always successful in eradicating the malignancy. Disadvantages of the use of such seeds as radiotherapy devices typically include their nature as discrete sources of radiation, and the corresponding discrete nature of the dosages that they provide. To provide an effective radiation dose over an elongated or wide target area, the seeds should be uniformly and relatively closely spaced. The need to ensure accurate and precise placement of numerous individual radiation sources undesirably prolongs the exposure of the medical operator and the surgical team to radiation. Moreover, the use of discrete seeds requires an elaborate grid matrix for their proper placement. This requirement is labor-intensive and costly. In addition, the discrete nature of the seeds renders them more susceptible to migration from their intended locations, thereby potentially subjecting portions of the lesion, the treatment site, and surrounding healthy tissue to over- or under-dosage, reducing the effectiveness and reliability of the therapy.

In an attempt to accomplish a more even distribution of radioactive seeds in a longitudinal direction, the so-called "rapid strand" approach provides a bioabsorbable strand or suture onto which several radioactive seeds have been pre-assembled in a uniform spacing approximately 10 mm apart. Unfortunately, although spacing the seeds along the strand can generally provide a somewhat more uniform longitudinal radiation dosage to the patient, the strand itself may not be sufficiently rigid to allow for it to be properly and reliably installed at the treatment site without becoming jammed in the delivery needles. In addition, because the seeds are the source of the radiation, as mentioned above, the radiation dose provided thereby has the limitations associated with the discrete nature of the seeds.

Further, medical operators typically use 18-gauge bevel-tip needles to place brachytherapy seeds. Due to the bevel tip and flexibility of the hypodermic tubing of the 18-gauge needle, such needles tend to splay making it necessary for the medical operator to make multiple sticks to place the needle in the desired location.

SUMMARY OF THE INVENTION

It is an object of the invention to provide a medical device useful for delivering brachytherapy less invasively and more reliably than known systems and methods. Accordingly, a brachytherapy device including a radiation source and a multi-cannula delivery system for implantation of the radiation source into a body tissue site is disclosed herein.

According to one aspect of the present invention, in general, a tissue region is treated through introduction of a linear wire radiation source inside a body by means of a multi-cannula delivery system. Different configurations of the linear wire according to various embodiments of this aspect of the invention improve distribution of the radiation field, particularly in the longitudinal direction, and resistance to migration of the radiation source inside a patient's body. The multi-cannula delivery system provides for faster and more accurate placement of the radiation source. In particular, the multi-cannula delivery system is capable of penetrating tissue along a straighter path than the traditional needle delivery system having a bevel tip. Because the multi-cannula delivery system is stiffer than a traditional hollow needle, it retains its functionality even though the inner diameter of the delivery cannula is minimal and typically approximates the size of the radiation source.

In general, in one aspect, the invention features a brachytherapy device including a radiation source and a multi-cannula delivery system for implantation of the radiation source into a body tissue site. The radiation source comprises a radioactive material and is adapted for implantation into a body tissue site and for delivery of a predetermined dosage of radiation to the body tissue site. According to one embodiment of this aspect of the invention, the multi-cannula delivery system includes an outer cannula and an inner cannula having a distal tip and an outer diameter sufficiently small to fit inside the outer cannula.

In one embodiment of the invention, the inner cannula has an inner diameter sufficiently large to receive said radiation source therein. According to a further embodiment, the multi-cannula delivery system further includes an outer stylet having a distal tip and an outer diameter sufficiently small to fit inside the outer cannula. According to an additional embodiment, the multi-cannula delivery system also includes an inner stylet having a distal tip and an outer diameter sufficiently small to fit inside the inner cannula.

According to various embodiments of the invention, the radiation source may include a substantially straight round wire, a substantially straight flat wire, a detented wire, an embossed wire, a bristled wire, a shaped resilient wire, a twisted round wire, a twisted flatwire, or a coil with an inner core. The radiation source may also include a coil of variable length.

In one embodiment of the invention, the outer cannula has an echogenic tip. In some embodiments, the inner cannula may be preloaded with the radiation source. According to one feature of the invention, the distal tip of the inner cannula is plugged. According to another feature, the distal tip of the inner stylet has a blunt flat tip.

In one embodiment of the invention, the outer cannula and the inner cannula have longitudinal openings. According to one feature, the inner cannula may be capable of rotating in relation to the outer cannula so as to cause these longitudinal openings to align. According to a further feature, the radiation source is releasable from the multi-cannula delivery system upon alignment of these longitudinal openings.

In one embodiment of the invention, the distal tip of the inner cannula includes a Huber point. In an alternative embodiment, the distal tip of the inner cannula includes a trocar. According to one version of this embodiment, the inner cannula has an eccentric opening at the distal tip. According to alternative version of this embodiment, the inner cannula has a side opening proximal to the distal tip.

In some embodiments of the invention, the brachytherapy device further includes a multi-cannula delivery system loading device, which includes a base, a container attached to the base and adapted for dispensing the radiation source therefrom, and a discharge tube attached to the base and adapted for receiving the radiation source dispensed from the container and for loading the radiation source into the multi-cannula delivery system. In one embodiment, the base defines a groove longitudinally formed therein. According to one feature, the radiation source is dispensed from the container into the groove. In a further embodiment, the discharge tube is disposed in the groove. Optionally, the discharge tube has a drop-in slot for receiving the radiation source therein.

According to one feature, the discharge tube also includes an actuator and a luer port for loading the radiation source into the multi-cannula delivery system. Optionally, the base may be adapted to facilitate cutting the radiation source within the groove. The base may also include a cutoff scale. According to another feature of the invention, the container is replaceable with other containers of various configurations.

The above and further objects, aspects, features, and advantages of the invention may be better understood by referring to the following description and from the claims.

BRIEF DESCRIPTION OF THE DRAWINGS

In the drawings, like elements are referenced with like reference designations throughout the different views. Also, depicted elements may not be drawn to scale, emphasis instead generally being placed upon illustrating the principles of the invention.

FIG. 5A shows a cross-sectional view taken along a longitudinal axis of an inner cannula of the multi-cannula delivery system of FIG. 1A having a trocar at its distal end according to an illustrative embodiment of the invention;

FIG. 5B shows a front end view of the inner cannula of FIG. 5A;

FIG. 5C shows a cross-sectional side view taken along a longitudinal axis of an inner cannula of the multi-cannula delivery system of FIG. 1A having a Huber point at its distal end, according to another illustrative embodiment of the invention;

FIG. 6 shows a multi-cannula delivery system loading device according to an illustrative embodiment of the invention;

FIG. 7A shows a cassette adapted for handling a radiation source of the brachytherapy device of FIG. 1A, which may be employed with the multi-cannula delivery system loading device of FIG. 6, according to an illustrative embodiment of the invention;

FIG. 7B shows a cassette adapted for handling a radiation source of the brachytherapy device of FIG. 1A, which may be employed with the multi-cannula delivery system loading device of FIG. 6, according to another illustrative embodiment of the invention;

FIG. 7C shows a cassette adapted for handling a radiation source of the brachytherapy device of FIG. 1A, which may be employed with the multi-cannula delivery system loading device of FIG. 6, according to a further illustrative embodiment of the invention; and FIG. 7D shows a cassette adapted for handling a radiation source of the brachytherapy device of FIG. 1A, which may be employed with the multi-cannula delivery system loading device of FIG. 6, according to an additional illustrative embodiment of the present invention.

ILLUSTRATIVE DESCRIPTION

Figure 1A:
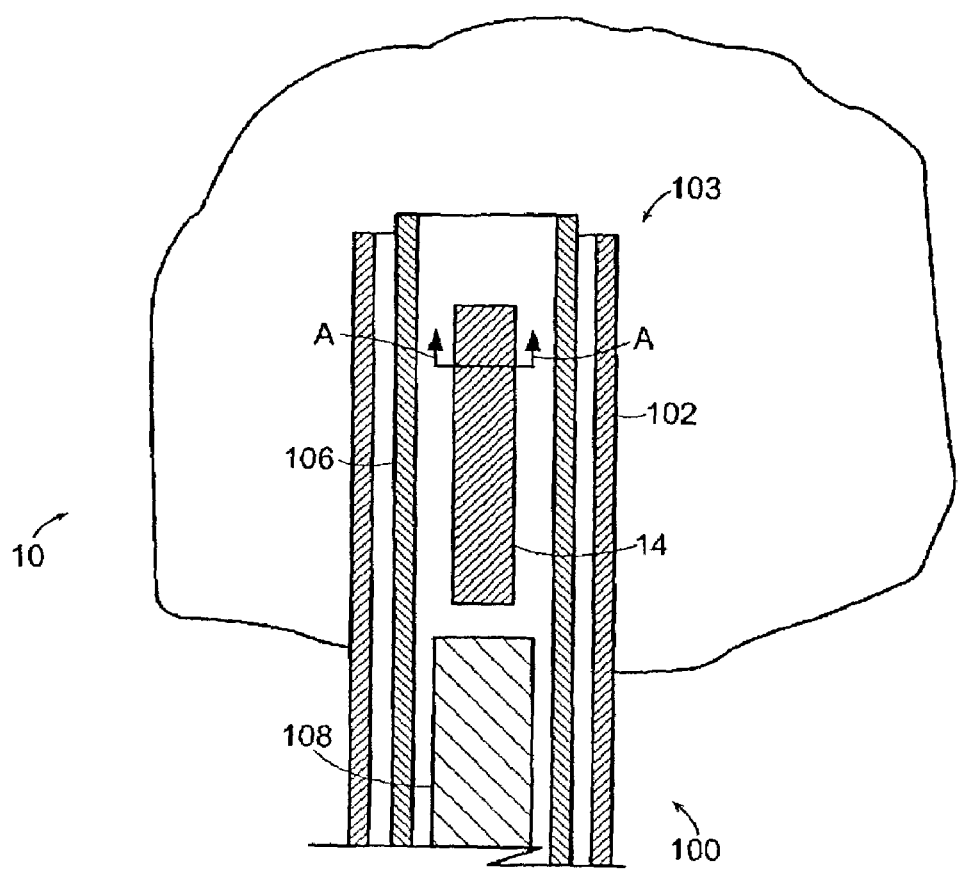
FIG. 1A depicts a brachytherapy device, including a multi-cannula delivery system loaded with a radiation source inserted to a body tissue site, according to an illustrative embodiment of the invention.

Referring to FIG. 1A, an illustrative brachytherapy device 10 includes a radiation source 14 loaded into a multi-cannula delivery system 100, which includes an outer cannula 102 and an inner cannula 106. The radiation source 14 can be made of, for example, iodine, iridium, palladium, or another suitable material that is radioactive. In a particular embodiment of the invention, the radiation source 14 is made of Rhodium, which becomes $^{103}$Pd (Palladium) after processing.

The multi-cannula delivery system 100 is inserted into a body tissue site 12. In the illustrative embodiment of FIG. 1A, the radiation source 14 is depicted as a substantially straight wire having a round outer surface. According to the illustrative embodiment of FIG. 1B, the diameter 15 of the radiation source 14 ranges from about 0.004 inches to about 0.010 inches depending, at least in part, upon the dose rates of the radiation source 14 and the desired dosage of radiation. However, according to the invention, the radiation source 14 may be formed in a variety of shapes and sizes without deviating from the scope of the invention.

Figure 1B:
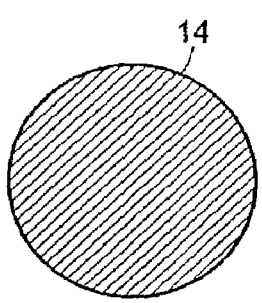
FIGS. 1B–1C show cross-sectional views, taken along the line AA, of two exemplary embodiments of the radiation source, which may be employed with the brachytherapy device of FIG. 1A.
Figure 1C:
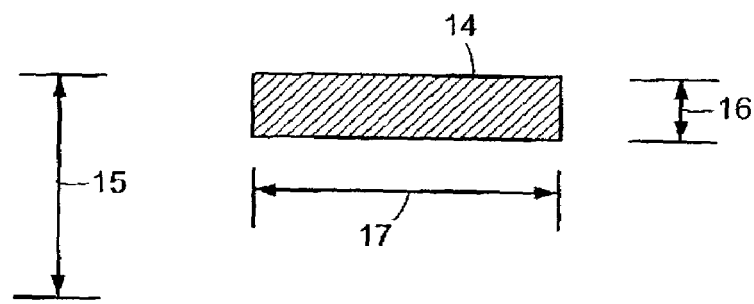

By way of example, in the illustrative embodiment of FIG. 1C, the radiation source 14 is formed as a substantially straight wire having at least one substantially flat surface. More particularly, the radiation source 14 is formed from a flat wire having a substantially rectangular cross-section, as shown in FIG. 1C. According to one feature, the substantially flat outer surface of the radiation source 14 improves its echogenicity to facilitate ultrasonic visualization of the multi-cannula delivery system during implantation of the radiation source 14. Preferably, the width 17 of the flat wire ranges from about 0.004 inches to about 0.010 inches with thickness 18 ranging from about 0.001 inches up to about 0.005 inches. However, other dimensions may be employed without deviating from the scope of the invention.

Figure 2A:
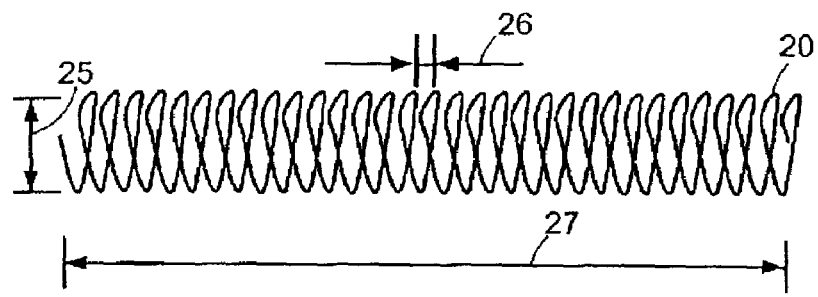
FIGS. 2A–2G show various illustrative radiation source configurations, which may be employed with the brachytherapy device of FIG. 1A.

FIGS. 2A–2G depict various illustrative configurations for the radiation sources 14, any of which may be employed with the brachytherapy device 10 of FIG. 1A. Referring to FIG. 2A, in another illustrative embodiment, the radiation source 14 is formed as a coil 20. The coil 20 may be open or closed. In one embodiment, the coil diameter 25 ranges from about 0.010 inches to about 0.031 inches, depending, at least in part, upon the dose rates of the radiation source, desired dosage of radiation, desired ultrasound echogenicity, and parameters of the delivery system. In a particular version of this embodiment of the invention, the coil diameter 25 is about 0.014 inches so that the coil 20 fits within a 23TW-gauge needle with inside diameter ranging from about 0.0165 inches to about 0.018 inches. The coil spacing 26 is up to about 0.002 inches depending, at least in part, upon the dose rates of the radiation source 14 and the desired dosage of radiation. In a particular embodiment of the invention, there is substantially no spacing between the coils of the radiation source 14. The coil length 27 ranges from about 5 mm to about 100 mm depending upon the size of the tissue at the treatment site. According to one illustrative embodiment, the number of coils used ranges up to about 30 depending, for example, on the size of the treatment region and the treatment configuration as determined by a physician.

Figure 2B:
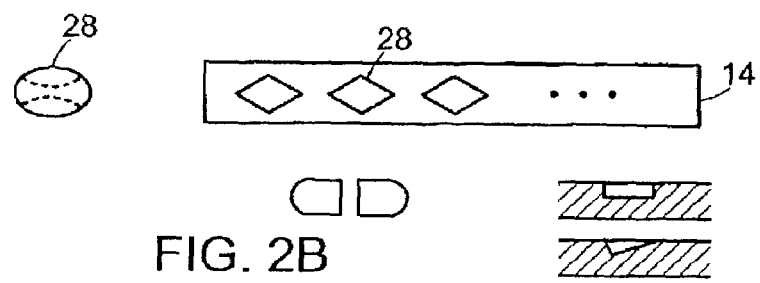
Figure 2C:
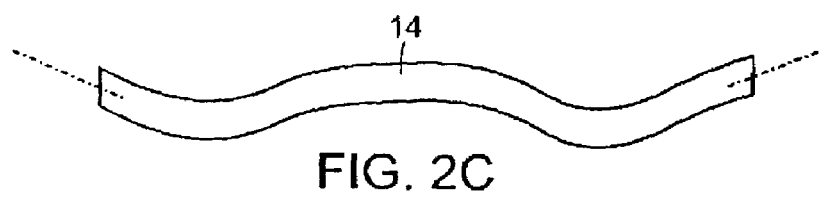
Figure 2D:
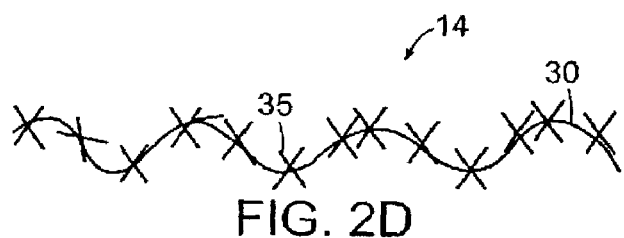
Figure 2E:
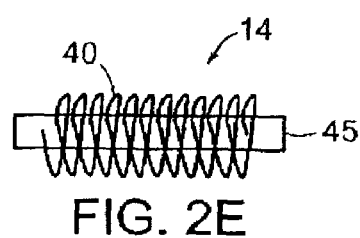
Figure 2F:
Figure 2G:
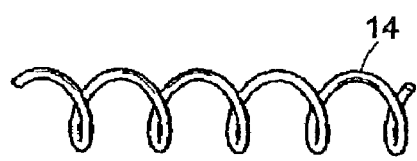

The radiation source 14 may be formed in other configurations, such as those shown in FIGS. 2B–2G. For example, the radiation source 14 may be a roll form wire with embossing or detents 28 on the surface, as shown in FIG. 2B. The radiation source 14, as shown in FIG. 2C, may be formed to have a structural resiliency that allows it to be delivered in a substantially straight form and to assume a serpentine form when placed in the body. Materials for achieving such structural resiliency are well known in the art. FIG. 2D depicts a radiation source 14 formed as a wire 30 having bristles 35 extending radially therefrom. Referring to FIG. 2E, a radiation source 14 comprises a coil 40 with a center core 45 that serves to stiffen the radiation source. The core 45 may comprise a radiopaque material to improve the visibility of the radiation source 14. In FIGS. 2F and 2G, the radiation source 14 is depicted in the shape of a twisted round wire and a twisted flat wire, respectively.

Each of the configurations of the radiation source 14 shown in FIGS. 2A–2G provides, as compared to the straight wire of FIGS. 1B and 1C, increased surface area and mass, without increasing the size of the radiation source 14. These configurations also improve resistance to migration of the radiation source 14 inside a body. In one embodiment, the length of the radiation source 14 varies depending upon the application and the size of the treatment site. For example, the radiation source 14 may be configured to be shorter where the treatment site is smaller. According to another illustrative feature, the radiation source 14 may be cut to an appropriate length prior to use through visual measurement or may be pre-cut to an appropriate size for a specific application.

In some illustrative embodiments, a single radiation source is employed. However, other illustrative embodiments employ multiple radiation sources. For example, when treating prostate cancer or benign prostate hyperplasia (BPH), a single radiation source may be used per lobe. Alternatively, in other configurations, up to three or more radiation sources may be used per lobe.

In one illustrative embodiment of the invention, the radiation source 14 may also be used for treating tissue through induction heating, for example, after a desired dose of radiation has been delivered. In this embodiment, the radiation material of the radiation source 14 is magnetically conductive. In operation, subsequent to inserting the magnetically conductive radiation source into the tissue at the treatment site, an electrically conductive inductor, such as, for example, a radio-frequency coil is inserted inside a body in close proximity to the treatment site, for example, through the urethra. Then, an alternating current is applied to the inductor to generate an electromagnetic field and to induce a current flow in the magnetically conductive radiation source to ablate the tissue.

Referring back to FIG. 1A, the illustrative brachytherapy device 10 of the invention further includes a multi-cannula delivery system 100 for delivering the radiation source 14 to the body tissue site 12. In an illustrative embodiment, the multi-cannula delivery system 100 includes an outer cannula 102, an inner cannula 106, and an inner stylet 108. According to one feature, the radiation source 14 can be preloaded into the inner cannula 106 prior to insertion of the inner cannula 106 into the desired body tissue site 12. According to another feature, the radiation source 14 may be loaded in the inner cannula 106 subsequent to inserting the inner cannula 106 into the body.

Still referring to FIG. 1A, in operation, the radiation source 14 is discharged from the inner cannula 106 and implanted into the body tissue site 12. Subsequent to inserting the radiation source 14 into the inner cannula 106, a medical operator positions the inner stylet 108 in the inner cannula 106 to maintain the position of the radiation source 14 when the outer cannula 102 and the inner cannula 106 are withdrawn over the inner stylet 108. After the radiation source 14 is implanted, the medical operator removes the outer cannula 102, the inner cannula 106, and the inner stylet 108 from the body. In an illustrative embodiment, the medical operator implants the radiation source 14 into the body tissue site 12 under ultrasound visualization. In this embodiment, at least a portion of the multi-cannula delivery system 100 is formed to be substantially echogenic, for example, by creating a textured or rough surface, or by including bubbles or fluid therein. According to one feature, a distal end 103 of the outer cannula 102 is formed to be substantially echogenic.

Figure 3A:
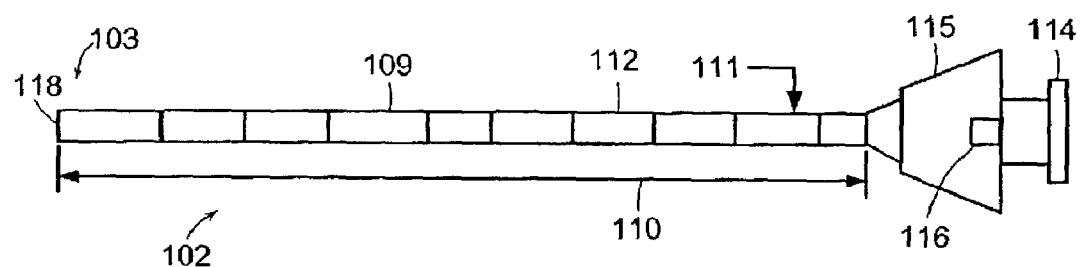
FIG. 3A shows an outer cannula, which may be employed with the multi-cannula delivery system of FIG. 1A.
Figure 3B:
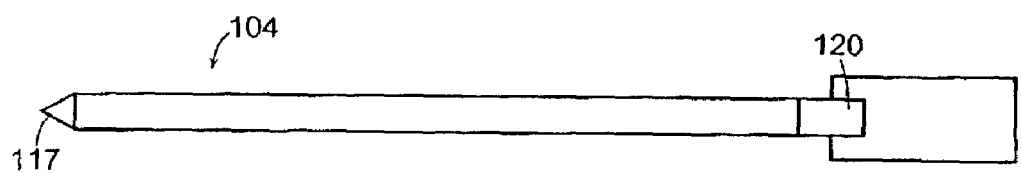
FIG. 3B shows an outer stylet of the multi-cannula delivery system of FIG. 1A, adapted for insertion into the outer cannula of FIG. 3A.

FIGS. 3A–3D depict various illustrative components of the multi-cannula delivery system 100. Referring to FIG. 3A, the system 100 includes an outer cannula 102. In one illustrative embodiment, the outer cannula 102 has an 18-gauge standard-wall hypodermic tube 109. In an alternative illustrative embodiment, the outer cannula 102 has a 19-gauge thin-wall hypodermic tube 109. In one illustrative embodiment, the length 110 of the tube 109 ranges from about 7 to about 10 inches. In a particular embodiment of the invention, the tube 109 is about 8 inches long. Optionally, the outer cannula 102 also has a lubricious coating on the outer surface 111 to reduce friction during insertion to the patient's body. Also, optionally, the outer cannula 102 includes distance markings 112 thereon to facilitate visual control over accuracy of placement during the insertion. Referring to FIGS. 3A and 3B, in one illustrative embodiment, the outer cannula 102 further includes a female luer fitting 114 on a hub 115 and a notch 116, for receiving a hub key 120 of the outer stylet 104. In some embodiments, at least a portion of the outer cannula 102 is substantially echogenic. By way of example, the outer cannula 102 may have an echogenic distal tip 103 to facilitate ultrasound visualization.

Referring to FIG. 3B, in one illustrative embodiment, the system 100 also includes the outer stylet 104 adapted to fit inside the outer cannula 102. In one illustrative embodiment, the outer stylet 104 has a distal cutting tip 117, such as a trocar or a tapered tip. According to one feature, the outer stylet 104 has the hub key 120 to mate with the notch 116 of the outer cannula 102, thereby enabling locking of the outer stylet 104 to the outer cannula 102.

Figure 3C:
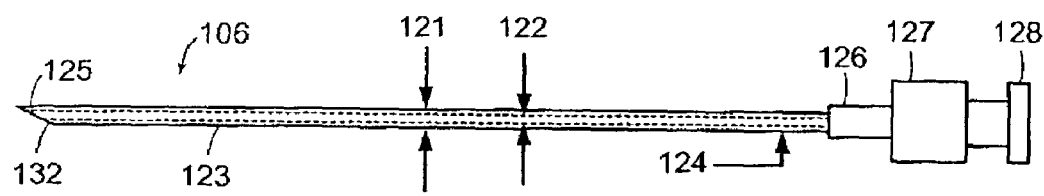
FIG. 3C shows an inner cannula of the multi-cannula delivery system of FIG. 1A, adapted for insertion into the outer cannula of FIG. 3A.

Referring to FIG. 3C, as described above with respect to FIG. 1A, the system 100 includes the inner cannula 106 adapted to fit inside the outer cannula 102 when the outer stylet 104 is removed therefrom. The outer diameter 121 of the inner cannula 106 is sufficiently small so that the inner cannula 106 may fit smoothly inside the outer cannula 102. In some embodiments, the inner cannula 106 has an inside diameter 122 sized to receive the radiation source 14 therein. In a particular embodiment, the inner cannula 106 includes a 22-gauge standard-wall hypodermic tube 123 having a substantially smooth inner surface 124. Optionally, the distal tip 125 of the inner cannula 106 is a bevel tip.

As shown in FIGS. 3A and 3C, according to an illustrative embodiment of the invention, the inner cannula 106 has a male luer fitting 126 on a hub 127 adapted to mate with the female luer fitting 114 on the hub 115 of the outer cannula 102. According to a further embodiment, the inner cannula 106 also has a female luer fitting 128 adapted to mate with the male luer 134 of the inner stylet 108, shown in FIG. 3D.

Figure 3D:
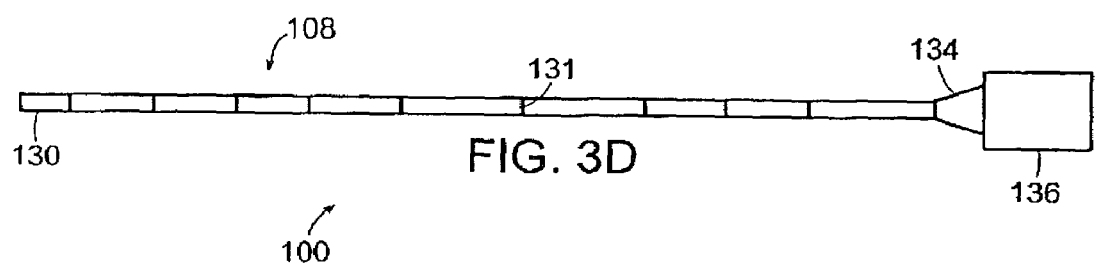
FIG. 3D shows an inner stylet of the multi-cannula delivery system of FIG. 1A, adapted for insertion into the inner cannula of FIG. 3C.

Referring to FIG. 3D, in the illustrative embodiment of the invention, the system 100 further includes the inner stylet 108 adapted to fit inside the inner cannula 106. According to one feature, the inner stylet 108 has a blunt distal tip 130. Optionally, the inner stylet 108 has distance markings 131 thereon. The inner stylet 108 may also have a male luer fitting 134 on a hub 136 to mate with the female luer fitting 128 of the inner cannula 106.

Figure 4A:
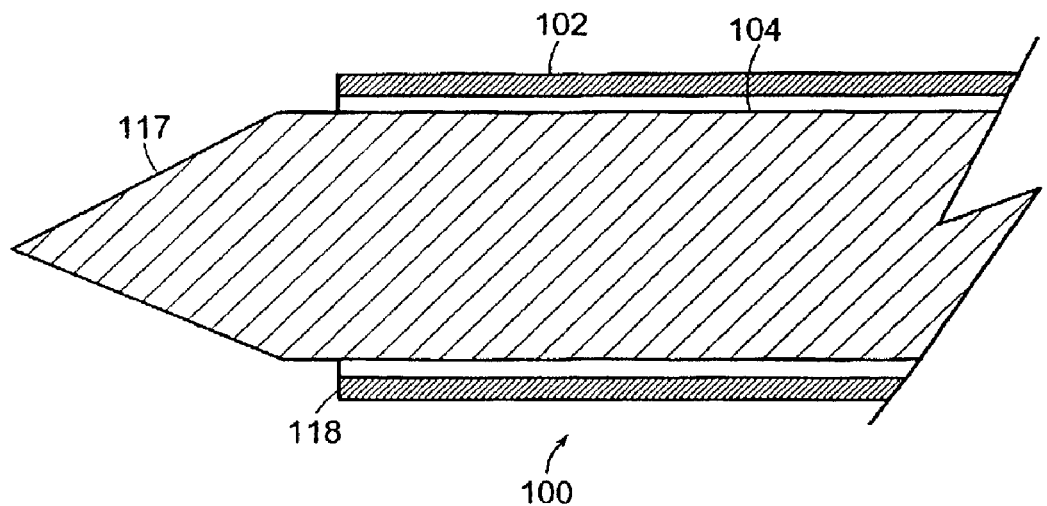
FIG. 4A is a cross-sectional view of the distal end of the multi-cannula delivery system of FIG. 1A taken along a longitudinal axis and depicting the outer stylet of FIG. 3B inserted into the outer cannula of FIG. 3A, according to an illustrative embodiment of the invention.

FIG. 4A depicts a portion of the outer stylet 104 of FIG. 3B inserted into the outer cannula 102 of FIG. 3A according to an illustrative embodiment of the invention. Referring to FIG. 4A, in operation, a medical operator places the outer stylet 104 into the outer cannula 102 and then inserts the outer cannula 102 with the outer stylet 104 locked therein into the desired treatment site. The outer stylet 104 is preferably longer than the outer cannula 102, so that the distal end 117 of the outer stylet 104 protrudes beyond the distal opening 118 of the outer cannula 102. Subsequent to inserting the outer cannula 102, with the outer stylet 104 locked therein, into the desired treatment site, the medical operator removes the outer stylet 104 from the outer cannula 102.

Figure 4B:
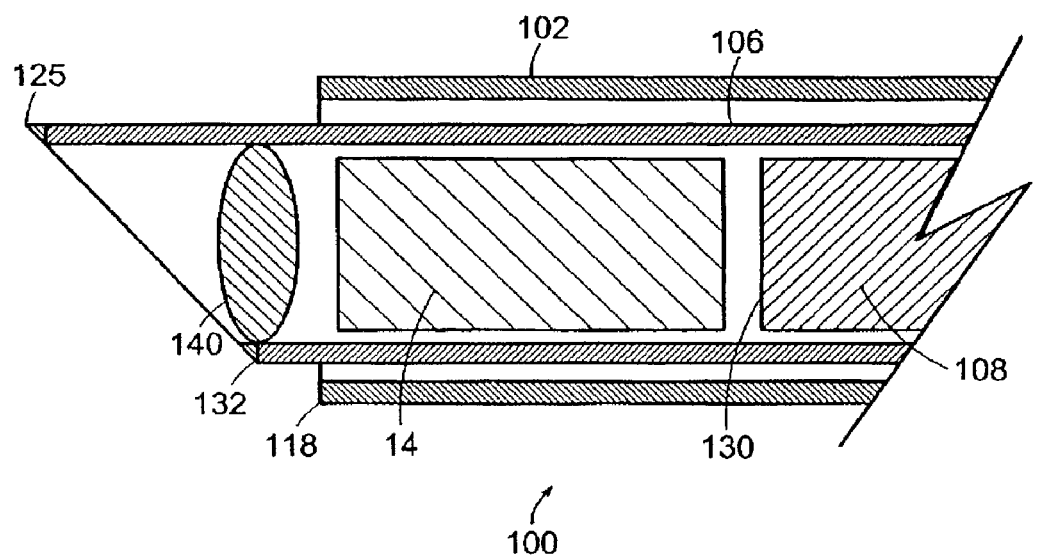
FIG. 4B is a cross-sectional view of the distal end of the multi-cannula delivery system of FIG. 1A taken along a longitudinal axis and depicting the inner cannula of FIG. 3C having an illustrative radiation source of FIGS. 2A–2G and the inner stylet of FIG. 3D placed therein and inserted into the outer cannula of FIG. 3A, according to an illustrative embodiment of the invention.

FIG. 4B depicts the inner cannula 106 of FIG. 3C having an illustrative radiation source of the type depicted in FIGS. 1B–2G and the inner stylet of FIG. 3D placed therein inserted in the outer cannula of FIG. 3A, according to an illustrative embodiment of the invention. Referring to FIG. 4B, in some embodiments, a medical operator loads the radiation source 14 inside the inner cannula 106 in advance of the insertion inside the body, so that the inner cannula 106 having the radiation source 14 therein is stored prior to the procedure. In other embodiments, the medical operator loads the radiation source 14 into the inner cannula 106 immediately prior to implantation. According to one feature, the radiation source 14 is loaded when the inner cannula 106 is substantially within the patient's body. In some embodiments, the radiation source 14, cut to a desired length, is loaded inside the inner cannula 106 using a pair of tweezers. In other embodiments, the radiation source 14, cut to a desired length, can be loaded inside the inner cannula 106 using a multi-cannula delivery system loading device, an illustrative embodiment of which is shown in FIG. 6.

As shown in the illustrative embodiment of FIG. 4B, the length of the inner cannula 106 is sufficient to allow the distal tip 125 to protrude slightly past the distal opening 118 of the outer cannula 102 when the inner cannula 106 is coupled to the outer cannula 102. Optionally, the distal tip 125 of the inner cannula 106 can be plugged with a bone wax 140. According to one feature, the inner stylet 108 is dimensioned so that its distal tip 130 protrudes past a proximal edge 132 of the distal tip 125 of the inner cannula 106.

Referring back to FIG. 4A, as mentioned above, in operation, the medical operator assembles the outer cannula 102 and the outer stylet 104, and then transperineally inserts the assembly into the patient's body under ultrasound visualization proximal to a tissue region to be treated, such as the prostate. During implantation, the cutting tip 117 of the outer stylet 104 penetrates tissue. After desired placement inside the body, the outer stylet 104 is unlocked and removed from the outer cannula 102 and the patient's body.

According to the illustrative embodiment of FIG. 4B, subsequent to withdrawal of the outer stylet 104, the medical operator inserts the inner cannula 106 having the radiation source 14 and the inner stylet 108 therein into the outer cannula 102. The inner stylet 108 is placed inside the inner cannula 106 so that it is in contact with the radiation source 14.

Still referring to FIG. 4B, according to one feature of the invention, the medical operator then pushes the radiation source 14 towards the distal tip 125 of the inner cannula 106 using the inner stylet 108 until the radiation source 14 begins to push out the bone wax 140. Then, the medical operator typically applies pressure to the inner stylet 108 to hold the radiation source 14 in place while he or she withdraws the inner cannula 106 and the outer cannula 102 from the treatment site over the inner stylet 108 to expose the radiation source 14, as observed by the ultrasound equipment. The illustrative implantation process concludes with a removal of the inner stylet 108 from the patient's body.

As depicted in FIGS. 5A–5E, the multi-cannula delivery system 100 employ a variety of inner cannula 106 configurations without deviating from the scope of the invention. By way of example, the inner cannula 106 of FIGS. 5A and 5B has a trocar point 208 and an eccentric bore 210 at the distal tip 125. The bore 210 has an opening 211 on one face 212 of the trocar point 208. According to one feature, the trocar point 208 improves tissue penetration during insertion. More specifically, when inserted into a tissue, for example, a prostate, the inner cannula 106 of this embodiment of the invention is less likely to splay as compared to an inner cannula having, for example, a bevel tip.

According to the illustrative embodiment of FIG. 5C, the inner cannula 106 has a Huber point 213 at the distal tip 125. The Huber point 213 is formed by bending the tip of the inner cannula 106 so that the opening 214 of the bore 216 appears to be through the side of the cannula 106. Because the opening 214 is provided only on a side of the cannula 106, the Huber point 213 improves insertion by reducing tissue penetration into the bore 216. In this embodiment, the penetrating Huber point 213 falls on the central axis 215 of the inner cannula 106 to reduce splaying when the inner cannula 106 is placed inside tissue. According to one feature of the invention, because of its flexibility, the radiation source 14 (not shown) exits the bore 216 through the opening 214.

Figure 5D:
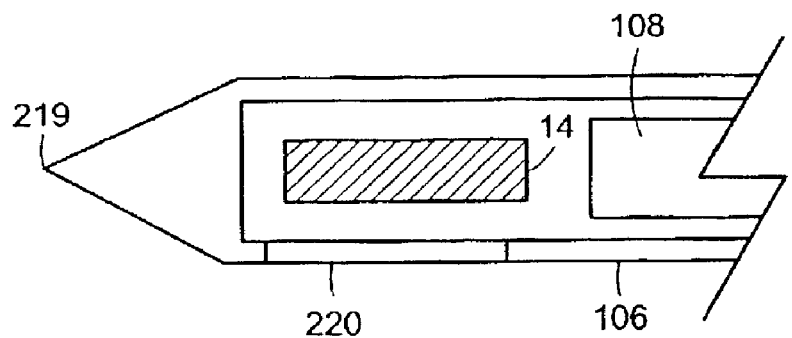
FIG. 5D shows a cross-sectional side view taken along a longitudinal axis of an inner cannula of the illustrative multi-cannula delivery system of FIG. 1A having a trocar point and a side opening at its distal end, according to a further illustrative embodiment of the invention.

According to the illustrative embodiment shown in FIG. 5D, the inner cannula 106 has a trocar point 219 and a side opening 220 in the side wall of the inner cannula 106. In this embodiment, the trocar point 219 is solid, which generally facilitates tissue penetration. In operation, the radiation source 14 is released through the side opening 220 using the inner stylet 108.

Figure 5E:
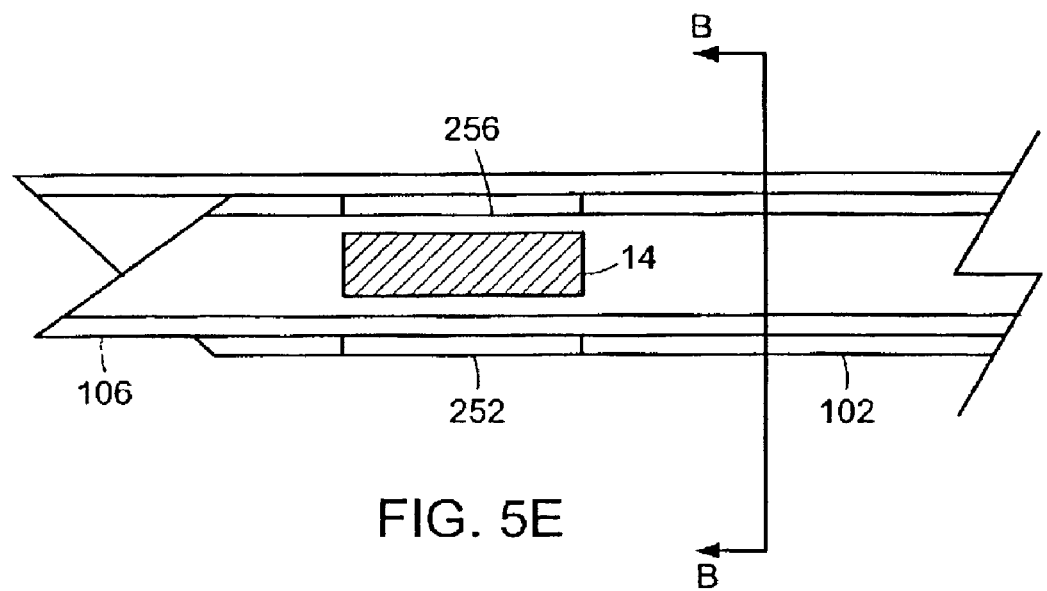
FIG. 5E shows a cross-sectional side view taken along a longitudinal axis of an outer cannula and an inner cannula of the multi-cannula delivery system of FIG. 1A each having side openings at their respective distal ends according to an additional illustrative embodiment of the invention.
Figure 5F:
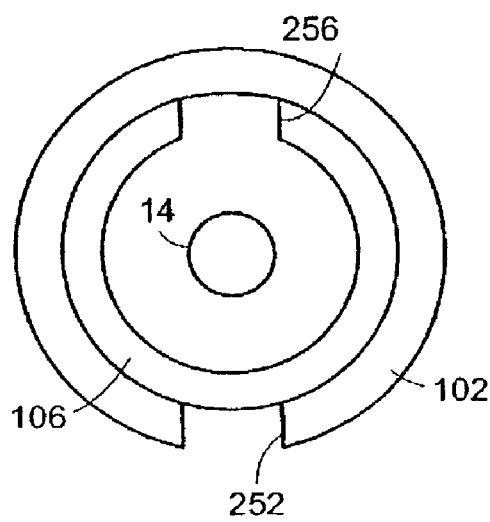
FIG. 5F shows a cross-sectional view taken along the line BB of the inner cannula and the outer cannula of FIG. 5E in a closed position.
Figure 5G:
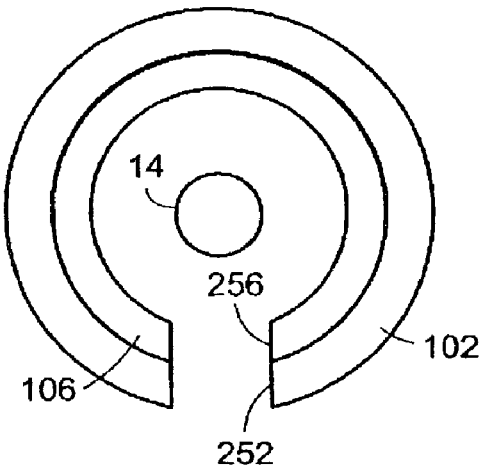
FIG. 5G shows a cross-sectional view taken along the line BB of the inner cannula and the outer cannula of FIG. 5E in an open position.

According to the illustrative embodiment shown in FIGS. 5E–5G, the outer cannula 102 and the inner cannula 106 have longitudinal openings 252 and 256 respectively at their respective distal ends. The openings 252, and 256 are located in side walls of the outer cannula 102 and the inner cannula 106 proximal to the distal ends thereof. The inner cannula 106 is generally capable of rotation relative to the outer cannula 102 so as to cause the longitudinal openings to substantially align. According to one feature of the invention, the openings 252 and 256 are dimensioned to control release of the radiation source 14 in a desired orientation. When the opening 252 of the outer cannula 102 and the opening 256 of the inner cannula 106 are substantially aligned as shown in FIG. 5G, the radiation source 14 inside the inner cannula 106 is released. After the radiation source 14 is released through the openings 252 and 256, as observed by the ultrasound equipment, the outer cannula 102, the inner cannula 106, and the inner stylet 108 are removed from the body.

As shown in FIG. 5E, in one illustrative embodiment of the invention, the outer cannula 102 and the inner cannula 106 each has a 45-degree bevel cutting tip at their respective distal ends. When the outer cannula 102 and the inner cannula 106 loaded with the radiation source 14 are inserted inside the body, the openings 252 and 256 are placed opposite each other (see FIG. 5F) and a substantially closed tube with a conical cutting tip is formed. When the medical operator rotates the outer cannula 102 and the inner cannula 106 relative to one another to align the openings 252 and 256, the distal tip of the inner cannula 106 rests inside the tip of the outer cannula 102.

The radiation source can be loaded into a multi-cannula delivery system in a variety of ways. According to the illustrative embodiment of FIG. 6, the radiation source 14 in a shape of a coil 72 is loaded in the following manner. A round container 74 containing the coil 72 therein is attached to a base 71 of a multi-cannula delivery system loading device 70 shown in FIG. 6. In other embodiments, various wire cassettes such as a spool, a cartridge and a feed screw shown in FIGS. 7A–7D can be attached to the base 71 of the multi-cannula delivery system loading device 70 to replace the container 74.

In operation, a medical operator feeds a loose end of the coil 72 through a lead hole 76 into a groove 78 formed in the base 71. Using a pair of tweezers or other suitable mechanism, the medical operator grasps the end of the coil 72 and pulls it out to a desired length. In one embodiment, the length of the coil 72 is measured using a cutoff scale 79. Using a pair of scissors or other suitable mechanism, the medical operator cuts the coil 72 at the location of the cutting slot 80. The coil 72 is released and dropped through a loading slot (not shown) into a discharge tube 86 axially disposed in the groove 78. Then, the medical operator inserts a female luer port of the multi-cannula delivery system (not shown) into a male luer port 84 at the end of the discharge tube 86. By applying pressure to the coil 72, the medical operator transfers the coil 72 from the discharge tube 86 into the multi-cannula delivery system 100 through the luer port 84. Then, the multi-cannula delivery system 100, with the loaded radiation source, is removed from the loading device 70. In one illustrative embodiment of the invention, the medical operator applies pressure to the coil 72 in the discharge tube 86 using an actuator, for example, a plunger 88 shown in FIG. 6. Other pressurizing mechanisms known in the art may be employed instead of the plunger 88 without deviating from the scope of the invention.

Variations, modifications, and other implementations of what is described herein will occur to those of ordinary skill in the art without departing from the spirit and the scope of the invention as claimed. Accordingly, the invention is to be defined not by the preceding illustrative description but instead by the spirit and scope of the following claims and all equivalents thereof.

What is claimed is:

1. A brachytherapy device for release of a radiation source within a body tissue site, comprising:
    an implantable radiation source comprising a radioactive material, said radiation source adapted for implantation into a body tissue site and for delivery of a dosage of radiation to said body tissue site; and
    a multi-cannula delivery system for implantation of said radiation source into said body tissue site, comprising an outer cannula and an inner cannula adapted to fit within the outer cannula wherein said outer cannula and said inner cannula comprise longitudinal openings such that rotation of said inner cannula in relation to said outer cannula causes said longitudinal openings to align and said radiation source is releasable from said multi-cannula delivery system upon alignment of said longitudinal openings, wherein said radiation source comprises a coil.

2. The device of claim 1 wherein said coil has a variable length and an inner core.

3. A brachytherapy device for release of a radiation source within a body tissue site, comprising:
    an implantable radiation source comprising a radioactive material, said radiation source adapted for implantation into a body tissue site and for delivery of a dosage of radiation to said body tissue site; and
a multi-cannula delivery system for implantation of said radiation source into said body tissue site, comprising an outer cannula and an inner cannula adapted to fit within the outer cannula wherein said outer cannula and said inner cannula comprise longitudinal openings such that rotation of said inner cannula in relation to said outer cannula causes said longitudinal openings to align and said radiation source is releasable from said multi-cannula delivery system upon alignment of said longitudinal openings, wherein said inner cannula has a distal tip and an outer diameter sufficiently small to fit inside said outer cannula and further comprising an outer stylet having a distal tip and an outer diameter sufficiently small to fit inside said outer cannula.

4. A brachytherapy device for release of a radiation source within a body tissue site, comprising:
    an implantable radiation source comprising a radioactive material, said radiation source adapted for implantation into a body tissue site and for delivery of a dosage of radiation to said body tissue site; and
a multi-cannula delivery system for implantation of said radiation source into said body tissue site, comprising an outer cannula and an inner cannula adapted to fit within the outer cannula wherein said outer cannula and said inner cannula comprise longitudinal openings such that rotation of said inner cannula in relation to said outer cannula causes said longitudinal openings to align and said radiation source is releasable from said multi-cannula delivery system upon alignment of said longitudinal openings, wherein said inner cannula has a distal tip and an outer diameter sufficiently small to fit inside said outer cannula and further comprising an inner stylet having a distal tip and an outer diameter sufficiently small to fit inside said inner cannula.

5. A brachytherapy device for release of a radiation source within a body tissue site, comprising:
    an implantable radiation source comprising a radioactive material, said radiation source adapted for implantation into a body tissue site and for delivery of a dosage of radiation to said body tissue site; and
a multi-cannula delivery system for implantation of said radiation source into said body tissue site, comprising an outer cannula and an inner cannula adapted to fit within the outer cannula wherein said outer cannula and said inner cannula comprise longitudinal openings such that rotation of said inner cannula in relation to said outer cannula causes said longitudinal openings to align and said radiation source is releasable from said multi-cannula delivery system upon alignment of said longitudinal openings, further including a multi-cannula delivery system loading device, comprising:
    a base,
    a container attached to said base and adapted for dispensing said radiation source therefrom, and
    a discharge tube attached to said base and adapted for receiving said radiation source dispensed from said container and for loading said radiation source into said multi-cannula delivery system, wherein said container is removably and reusably attached to said base.

6. A brachytherapy device for release of a radiation source within a body tissue site, comprising:
    an implantable radiation source comprising a radioactive material, said radiation source adapted for implantation into a body tissue site and for delivery of a dosage of radiation to said body tissue site; and
a multi-cannula delivery system for implantation of said radiation source into said body tissue site, comprising an outer cannula and an inner cannula adapted to fit within the outer cannula wherein said outer cannula and said inner cannula comprise longitudinal openings such that rotation of said inner cannula in relation to said outer cannula causes said longitudinal openings to align and said radiation source is releasable from said multi-cannula delivery system upon alignment of said longitudinal openings, further including a multi-cannula delivery system loading device, comprising:
    abase,
    a container attached to said base and adapted for dispensing said radiation source therefrom, and
    a discharge tube attached to said base and adapted for receiving said radiation source dispensed from said container and for loading said radiation source into said multi-cannula delivery system, wherein said discharge tube is removably and reusably attached to said base.

7. A brachytherapy device for release of a radiation source within a body tissue site, comprising:
    an implantable radiation source comprising a radiation material, said radiation source adapted for implantation into a body tissue site and for delivery of a dosage of radiation to said body tissue site;

a multi-cannula delivery system for implantation of said radiation source into said body tissue site, comprising an outer cannula and an inner cannula adapted to fit within the outer cannula wherein the radiation source is removable from the device by release from an opening in the inner cannula; and a multi-cannula delivery system loading device, comprising: a base, a container attached to said base and adapted for dispensing said radiation source therefrom, and a discharge tube attached to said base and adapted for receiving said radiation source dispensed from said container and for loading said radiation source into said multi-cannula delivery system, wherein said base further comprises a cutoff scale.

8. A brachytherapy device for release of a radiation source within a body tissue site, comprising:

an implantable radiation source comprising a radioactive material, said radiation source adapted for implantation into a body tissue site and for delivery of a dosage of radiation to said body tissue site; and a multi-cannula delivery system for implantation of said radiation source into said body tissue site, comprising an outer cannula and an inner cannula adapted to fit within the outer cannula wherein said outer cannula and said inner cannula comprise longitudinal openings such that rotation of said inner cannula in relation to said outer cannula causes said longitudinal openings to align and said radiation source is releasable from said multi-cannula delivery system upon alignment of said longitudinal openings, further including a multi-cannula delivery system loading device, comprising:

a base, a container attached to said base and adapted for dispensing said radiation source therefrom, and a discharge tube attached to said base and adapted for receiving said radiation source dispensed from said container and for loading said radiation source into said multi-cannula delivery system, wherein said discharge tube comprises an actuator and a luer port, said actuator and said luer port adapted for loading said radiation source into said multi-cannula delivery system.

9. A brachytherapy device for release of a radiation source within a body tissue site, comprising:

an implantable radiation source comprising a radioactive material, said radiation source adapted for implantation into a body tissue site and for delivery of a dosage of radiation to said body tissue site; and a multi-cannula delivery system for implantation of said radiation source into said body tissue site, comprising an outer cannula and an inner cannula adapted to fit within the outer cannula wherein said outer cannula and said inner cannula comprise longitudinal openings such that rotation of said inner cannula in relation to said outer cannula causes said longitudinal openings to align and said radiation source is releasable from said multi-cannula delivery system upon alignment of said longitudinal openings, wherein said implantable radiation source comprises a wire-shaped element comprising a coil.

10. A brachytherapy device for release of a radiation source within a body tissue site, comprising:

an implantable radiation source comprising a radioactive material, said radiation source adapted for implantation into a body tissue site and for delivery of a dosage of radiation to said body tissue site; and a multi-cannula delivery system for implantation of said radiation source into said body tissue site, comprising an outer cannula and an inner cannula adapted to fit within the outer cannula wherein said outer cannula and said inner cannula comprise longitudinal openings such that rotation of said inner cannula in relation to said outer cannula causes said longitudinal openings to align and said radiation source is releasable from said multi-cannula delivery system upon alignment of said longitudinal openings, wherein said radiation source comprises a coil, and wherein said coil has an inner core.

* * * * *

UNITED STATES PATENT AND TRADEMARK OFFICE
CERTIFICATE OF CORRECTION

PATENT NO.         : 7,041,047 B2
APPLICATION NO. : 10/264637
DATED              : May 9, 2006
INVENTOR(S)        : Barry N. Gellman et al.

It is certified that error appears in the above-identified patent and that said Letters Patent is hereby corrected as shown below:

Col. 3, line 59, before "alternative", insert -- an --.

Col. 12, line 56, change "abase" to -- a base --.

Signed and Sealed this

Twenty-sixth Day of December, 2006

JON W. DUDAS
*Director of the United States Patent and Trademark Office*